United States Patent
Cordero et al.

(10) Patent No.: US 8,700,122 B2
(45) Date of Patent: Apr. 15, 2014

(54) SKIN PREPARATION DEVICE AND BIOPOTENTIAL SENSOR

(75) Inventors: Rafael M. Cordero, Bedford, MA (US); Robert Harhen, Haverhill, MA (US); Melissa Kinney, Phoenix, AZ (US); Graham Houtchens, Natick, MA (US); Marc Davidson, Andover, MA (US); Rebecca Brumer, Arlington, MA (US)

(73) Assignee: Covidien LP, Mansfield, MA (US)

( * ) Notice: Subject to any disclaimer, the term of this patent is extended or adjusted under 35 U.S.C. 154(b) by 736 days.

(21) Appl. No.: 12/435,028

(22) Filed: May 4, 2009

(65) Prior Publication Data

US 2010/0022864 A1 Jan. 28, 2010

Related U.S. Application Data

(60) Provisional application No. 61/126,849, filed on May 2, 2008.

(51) Int. Cl.
*A61B 5/0408* (2006.01)
*A61B 5/04025* (2006.01)
*A61B 17/20* (2006.01)

(52) U.S. Cl.
USPC .............. 600/393; 600/382; 604/46

(58) Field of Classification Search
USPC ............ 600/372, 382–386; 607/116–118
See application file for complete search history.

(56) References Cited

U.S. PATENT DOCUMENTS

| | | | |
|---|---|---|---|
| 2,727,516 A * | 12/1955 | Lockhart | 600/578 |
| 2,943,628 A * | 7/1960 | Howell | 600/391 |
| 4,685,466 A | 8/1987 | Rau | |
| 4,709,702 A * | 12/1987 | Sherwin | 600/383 |
| 5,305,746 A | 4/1994 | Fendrock | |
| 5,309,909 A | 5/1994 | Gadsby et al. | |
| 6,032,064 A | 2/2000 | Devlin et al. | |
| 6,136,008 A | 10/2000 | Becker et al. | |
| 6,434,410 B1 * | 8/2002 | Cordero et al. | 600/396 |
| 6,510,333 B1 | 1/2003 | Licata et al. | |
| 6,622,035 B1 | 9/2003 | Merilainen et al. | |
| 6,690,959 B2 | 2/2004 | Thompson | |

(Continued)

FOREIGN PATENT DOCUMENTS

| JP | 2005334594 A * | 12/2005 |
|---|---|---|
| WO | WO-01/52731 | 1/2001 |

(Continued)

OTHER PUBLICATIONS

Microelectrode Arrays, Cyberkinetics—Neurotechnology Systems, Inc., dated Mar. 16, 2005 (2 pages), accessed from http://www.cyberkineticsinc.com/content/researchproducts/microelectrodearrays.jsp.

(Continued)

*Primary Examiner* — Linda Dvorak
*Assistant Examiner* — Brian M Antiskay

(57) ABSTRACT

The skin preparation device and sensor of the present invention include an array of rigid tines. The tines serve to "self-prepare" the skin at each electrode site. These tines, when pressed against the skin, penetrate the stratum corneum, thereby reducing skin impedance and improving signal quality. A self-prepping device of the present invention is an optimized array of short non-conductive rigid tines in which the individual tines are created in a geometry that allows for a sharp point at the tip when molding, machining or etching is used as a method of fabrication.

8 Claims, 8 Drawing Sheets

(56) References Cited

U.S. PATENT DOCUMENTS

| | | |
|---|---|---|
| 6,782,283 B2 | 8/2004 | Schmidt et al. |
| 6,785,569 B2 | 8/2004 | Schmidt et al. |
| 6,961,603 B2 | 11/2005 | Merilainen et al. |
| 7,013,179 B2 | 3/2006 | Carter et al. |
| 7,032,301 B1 | 4/2006 | Schmidt et al. |
| 7,032,302 B1 | 4/2006 | Schmidt et al. |
| 7,103,398 B2 | 9/2006 | Sieburg et al. |
| 7,316,671 B2 * | 1/2008 | Lastovich et al. ............ 604/290 |
| 2004/0054393 A1 * | 3/2004 | Stemme et al. .............. 607/149 |
| 2006/0173261 A1 | 8/2006 | Kall et al. |
| 2007/0276211 A1 | 11/2007 | Mir et al. |
| 2008/0009763 A1 * | 1/2008 | Chiou et al. ................. 600/544 |
| 2008/0139911 A1 | 6/2008 | Chandrasekaran et al. |
| 2008/0294031 A1 * | 11/2008 | Wilson et al. ............... 600/383 |
| 2009/0253975 A1 * | 10/2009 | Tiegs et al. .................. 600/372 |

FOREIGN PATENT DOCUMENTS

| | | |
|---|---|---|
| WO | WO-02/00096 | 1/2002 |
| WO | WO-2004/009172 | 1/2004 |
| WO | WO-2007/075614 | 7/2007 |
| WO | WO-2007/081430 | 7/2007 |

OTHER PUBLICATIONS

Sivamani, R.K. et al., "Microneedles and transdermal applications," Expert Opin. Drug Deliv., 4(1): 19-25 (2007).

Griss, P. et al., "Micromachined Electrodes for Biopotential Measurements," J. MicroElectroMech. Sys., vol. 10(1): 10-16 (2001).

Ng, W.C., et al., "Micro-spike EEG electrode and the vacuum-casting technology for mass production," J. Mater. Process. Tech., doi:10.1016/j.jmatprotec.2008.10.051, (5 pages) (2009).

International Search Report issued for PCT/US09/042684, dated Dec. 1, 2009 (3 pages).

* cited by examiner

SKIN PREPARATION DEVICE AND BIOPOTENTIAL SENSOR

CROSS REFERENCE TO RELATED APPLICATION

This application claims benefit of Provisional Application Ser. No. 61/126,849, filed on May 2, 2008.

BACKGROUND OF THE INVENTION

This invention relates to a skin preparation device that can be used to penetrate the outermost layer of skin to allow for the penetration and/or displacement of the stratum corneum. A typical use of such invention is in the non-invasive monitoring of electrophysiological signals. This skin preparation device may be integrated into the electrodes of a biopotential sensor.

The human skin tissue is composed primarily of connective tissue, the dermis, covered by a protective layer, the epidermis. The outermost layer of the epidermis is the stratum corneum. In the study of electrophysiological monitoring using surface electrodes, the stratum corneum is significant, due to its function as a protective barrier. The stratum corneum is on average approximately 20 µm thick, and is composed primarily of denucleated, dead skin cells that are inherently a source of high electrical impedance. Very low amplitude signals are associated with some electrophysiological recordings, particularly electroencephalography (EEG); therefore, it is important to optimize the signal acquisition and minimize noise artifact. Thus, impedance measured at the interface between a patient's skin and the electrode used for acquiring the electrophysiological signals is an important consideration in biopotential monitoring. Additionally, variance in impedance between electrode sites can result in unwanted noise in the signal. Good electrical conduction between the patient's skin and the electrode can be better achieved by removing or penetrating the stratum corneum layer of the epidermis.

The most common electrodes that are applied to the surface of the skin often require that the skin be prepared before the electrode is applied. Preparation of the skin typically begins with cleaning off the surface with alcohol to remove dirt and oils, followed by abrasion of the skin's surface with an abrasive material or a grit-impregnated gel to remove the stratum corneum layer. To simplify the skin preparation process that is required prior to application of an electrode, several forms of self-prepping electrodes have been developed. Such electrodes, which have an integrated mechanism for achieving this preparation of the skin, provide numerous advantages over standard EEG or electrocardiogram (ECG) electrodes because they eliminate the need for the additional step of skin preparation as well as the need to have the abrasive material available in a clinical setting.

In many of these developments, the means by which the skin preparation occurs is by employing a textured component in conjunction with the electrode, which when pushed against the skin attempts to abrade or penetrate the outermost layer. This textured component may be a part of the electrode surface itself or an independent part affixed to the electrode surface. International Patent Application WO 02/00096A2 describes a means of collecting EEG using a "volcano tip" tine structure, in which tines formed from perforations in the electrode material are used to abrade the outer layers of skin and improve electrical contact. This application does not describe the design or manufacturing procedures for the volcano tip tine structure.

U.S. Pat. No. 5,305,746 issued to Fendrock et al. describes an electrode which provides a textured component by way of an integrated array of non-conductive flexile tines. The flexile tines are of length 0.025"-0.110" and of thickness 0.002"-0.015", and are embedded in a wet conductive gel. The flexile tines part the stratum corneum layer to expose the low impedance layers without scratching or abrading deeper layers of the skin. Although this device does generally reduce the measured impedance at the skin to electrode (skin to gel) interface, the mechanism by which flexile tines part the skin varies from person to person and skin type to skin type. Long flexile tines lack uniformity of orientation and insertion angle into the skin. Rigid tines may provide better control over the tine orientation and the mechanism by which they bypass the stratum corneum. Due to their size, macro-sized tines, as described in U.S. Pat. No. 5,305,746, limit the potential density of the tines in the array thereby also limiting the ability to reduce the overall electrode size and overall area of skin that is affected while maintaining equivalent signal quality. In addition, long tines facilitate being pressed too deeply into the skin causing unnecessary penetration beyond the stratum corneum while a shorter tine limits the deformation of the skin. Consequently, the advantage of an array of shorter and more rigid tines is that they can produce more repeatable low impedance signals with potentially less irritation of the skin.

U.S. Pat. No. 5,309,909 issued to Gadsby discloses a skin preparation and monitoring electrode that penetrates a patient's skin prior to acquiring biopotentials. The electrode has tines, mounted on the concave surface of a dome, that penetrate first the conductive layer of the electrode and then the skin when force is applied to the dome causing it to deflect towards the skin. Upon cessation of the application of force, the tines retract with the movement of the dome. The complexity of this design does not support the cost effectiveness and ease of manufacturing required for a disposable electrode and skin preparation device.

The concept of using an array of shorter rigid tine structures for skin penetration is commonly associated with the applications of biopotential signal acquisition and transdermal drug delivery mechanisms. Among rigid tine array designs presented in journal and patent literature, there is a variety of tine array structures, materials, and dimensions, all optimized for their particular application.

International Patent Applications WO 2004009172A1, WO 2007075614A1, WO 2007081430A2 describe microneedle devices for delivering a drug to a patient via the skin. These needles typically have a channel through the middle allowing fluid to pass through the microneedle array or they are coated with a drug, or active component that is intended to dissolve in the skin beneath the stratum corneum. These needles for transdermal drug delivery have no conductive requirement because they do not serve to transmit any electrical signal away from the skin. These microneedles utilize lithographic processes on silicon in order to be created at such small scale.

An example of an additional application of an array of spikes used to achieve electrical contact with a series of very closely located electrode sites is described in U.S. Pat. No. 7,103,398 B2, issued to Sieburg. In this patent Sieburg describes a device for sensing electrical signals on the surface of human or animal skin. The device is comprised of a substrate containing a plurality of electrodes with each of those electrodes having one pointed contact end facing away from the substrate. In this design, each pointed contact, or "tine" is coupled electrically to an independent electrode site, rather than having multiple tines together penetrate an area of skin from which the signal will be conducted to the electrode surface.

U.S. Pat. No. 6,622,035, issued to Merilainen et al. also aims to effectively acquire biopotential signals with an electrode comprising an array of cylindrical or tapered "spikes" to make the skin more permeable. Each electrode is described as having 100-10,000 (ideally 400-2000) spikes per electrode, with the length of the spikes ranging from 50-250 μm (≤0.010") from the carrier or electrode surface. A subsequent patent, U.S. Pat. No. 6,961,603, also issued to Merilainen describes the same spike geometry and spike density; however such patent also teaches injection molding the "spikes" using a non-conductive material which will then be coated with a conductive layer such as silver-silver chloride. Such "spike" arrays, in addition to being conductive, are very small in size, fine in geometric characteristics and high in number spikes per array. These factors result in a non-cost effective design for molding, particularly for a disposable device.

U.S. Pat. No. 6,690,959, issued to Thompson also teaches the use of "nano-spikes" to penetrate the epidermis of the skin for collecting electrical biopotentials. The spikes are formed using a Microelectromechanical System (MEMs) construction technique and are subsequently coated with a conductive metal. Besides an indication that the nano-spikes are 10 μm in length and have an angularly disposed end shaped to assist in penetration of the cornified layer of the skin, no further detail regarding the geometry of the spikes is offered.

Similar biopotential signal acquiring devices have been created using carbon nanotubes. This approach is a highly effective means of creating very small, conductive tines in an array, however the cost and time associated with the growth of these arrays is currently prohibitive for integration into a high volume disposable product. The same drawbacks apply to microneedles formed using dry-etching of silicon, as it is a multi-step manufacturing process with high development costs.

One object of the proposed invention is the transduction of low impedance electrophysiological signals using a device that employs an array of sharp, rigid structures that can be integrated into a set of one of more electrodes to conduct the signals to a monitoring system. A further object is to provide a device that can be mass produced, for this application, at a cost appropriate for a disposable use product.

SUMMARY OF INVENTION

The device of the present invention includes an array of rigid tines. The tines serve to "self-prepare" the skin at each electrode site, providing for sufficiently low impedances required to collect high quality electrophysiological signals. These structures, when pressed against the skin (i.e. "prepping the skin"), penetrate the stratum corneum, thereby reducing skin impedance and improving signal quality. The function of this invention is to acquire repeatable bioelectrical signals with impedance less than 20 kΩ per electrode. These bioelectrical signals can then be transmitted from the electrode surface via the sensor conductors (leads) to the monitoring system. A self-prepping device of the present invention is an optimized array of short non-conductive rigid tines in which the individual tines are created in a geometry that allows for a sharp point at the tip when molding, machining or etching is used as a method of fabrication. This non-conductive array with rigid penetrating structures may, therefore, be used in combination with a conductive medium, preferably an ionic conductive gel. In penetrating the stratum corneum, micro-conduits are created in the layers of the skin enabling the conductive medium to reach the low impedance layers and to transmit bioelectrical signals from the skin to the electrode surface. Such a self-prepping device can be readily mass produced using molding methods or possibly other manufacturing methods, thereby providing for a low cost means of achieving improved performance of the biopotential sensor. Additionally this invention includes the integration of this self-prepping device into a biopotential sensor comprising an array of one or more electrodes.

The specific invention described herein of tines within a tine array, which can be integrated into the electrodes of a biopotential sensor, is optimized for performance in a specific application and additionally is optimized for successful and cost effective manufacturing by injection molding methods. An alternative method of manufacturing may include micromachining and resin casting from a mold. Post processes may include a vacuum depositioning of precious metals or conductive ink layering if a conductive part is desired.

DETAILED DESCRIPTION OF THE INVENTION

Figure 1A:
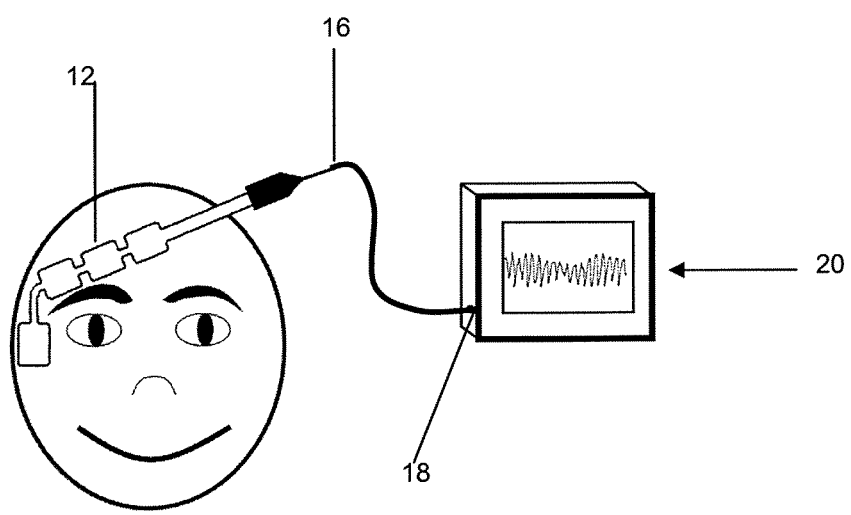
FIG. 1A is a schematic illustration of an embodiment of the sensor system in use.
Figure 1B:
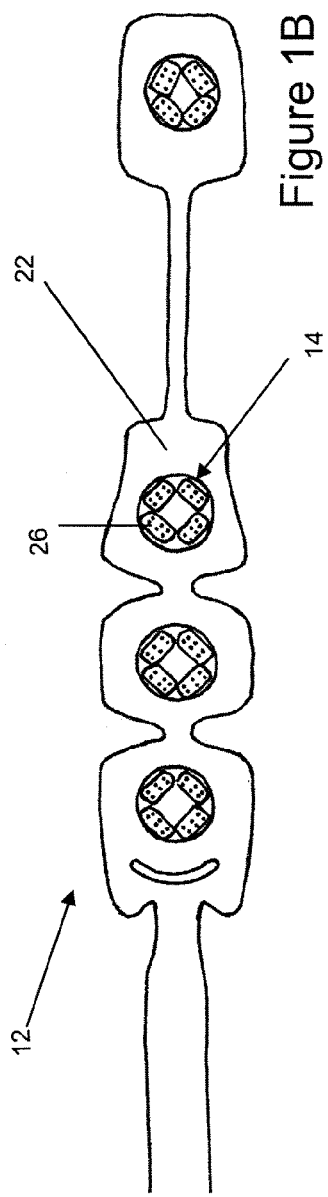
FIG. 1B is a top plan view of an embodiment of the sensor system

A biopotential sensor 12 shown in FIGS. 1A and 1B is a device that contains an array of one or more electrodes 14 and a set of conductors that provide an electrical conduction path for the acquired signals from the electrodes 14 to a single terminating connector 16 which in turn connects to the mating receptacle 18 of the biopotential monitoring system 20. The sensor device 12 may be coupled to the monitoring system via a terminating connector 16 inserted into a mating receptacle 18 on the monitoring system 20. Once electrical connection is achieved, the monitoring system 20 may perform analysis of the acquired biopotential signals.

The biopotential sensor 12 includes one or more electrodes 14. In the embodiment of the biopotential sensor 12 shown in FIG. 11B, the sensor 12 is comprised of four electrodes 14. In this embodiment, the sensor 12 includes a flexible substrate 22 with an adhesive layer on at least portions of the substrate 22 to enable secure placement on the skin. Not shown in the figure are the conductors which may be printed on the substrate 22 with conductive material or alternately be a set of conductive wires mounted on the substrate 22, and the terminating connector which enables connection of the conductors to the monitoring system. The electrodes 14 that comprise the sensor 12 may be formed with a layer of conductive material, preferably silver/silver chloride, which may be printed. Alternately the electrodes may incorporate a silver/silver chloride coated surface in contact with a post or stud on the opposite (non-patient contacting) surface. The post or stud makes electrical contact via a common EEG snap or a pre-attached wire, between the electrode surface and the conductors to the connector. The conductive surface of the electrode may also be formed of conductive carbon.

The surface of the electrode 14 may be coated with a conductive medium, preferably an ionic conductive wet gel, comparable to those commercially available for the application of signal acquisition. Alternately, a solid conductive gel may be used to coat the surface of the electrode 14. In another embodiment, the conductive gel may be both a conductive medium as well as an adhesive. The conductive gel provides continuous contact between the electrode surface and the surface of the skin even if the electrode substrate does not conform precisely to the curvature of the electrode site on the skin. In yet another embodiment the electrode 14 area may contain a sponge to keep the electrolytic gel in suspension.

Figure 1C:
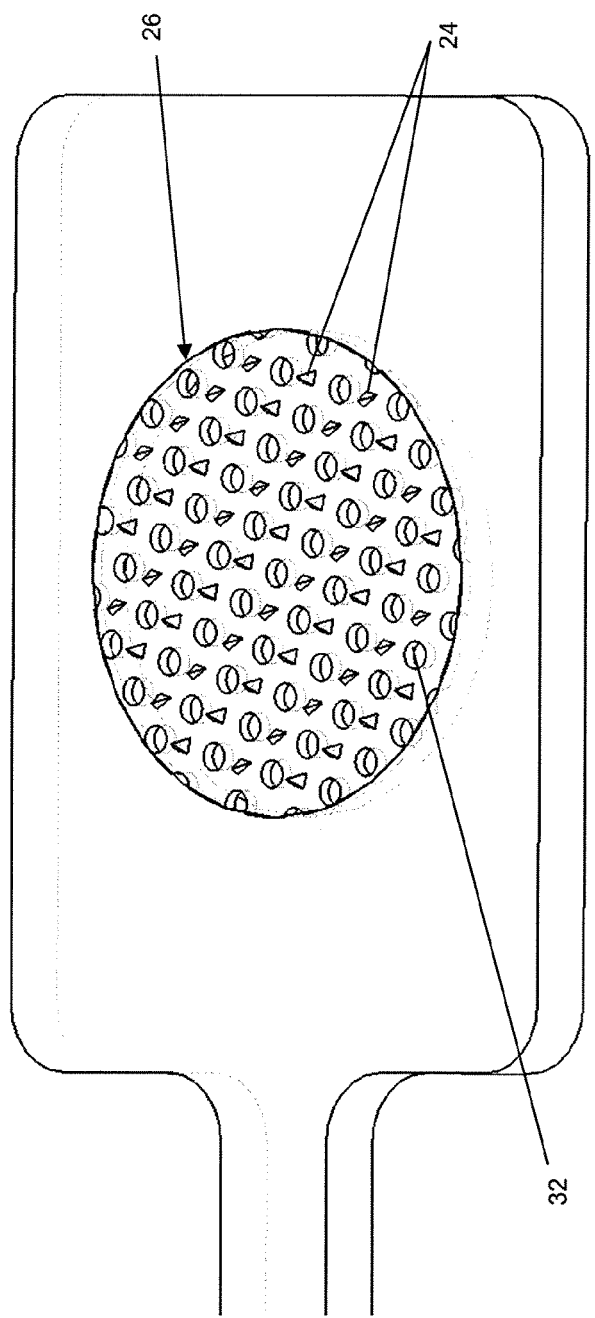
FIG. 1C is an enlarged perspective view of a skin preparation device incorporated in a sensor system.

Referring to FIG. 1C, included as part of the electrode 14 of this biopotential sensor 12 is a prepping device which is an array 26 of rigid tines 24. In one embodiment, the tine array 26, or multiple tine arrays, may be affixed to the electrode(s) 14 with an adhesive either on the bottom surface of the tine array 26 base or around its perimeter. The tine array 26 may be positioned such that a portion of the length of the tines 24 in a tine array 26 extends above the adhesive layer which may be on the flexible sensor substrate 22. In an alternate embodiment, the tine array 26 is not part of an array of electrodes 14, but instead is a separate component that is utilized to prepare the skin.

The rigid tines 24 may remain in contact with the skin and still remain affixed to the electrode surface once the electrode 14 with the prepping device on the sensor 12 has been pressed firmly against the skin. The tines 24 may retract from the skin once pressure is no longer being applied. In either arrangement pressing the electrode 14 toward the skin allows the tine structure to displace or penetrate the stratum corneum and allows the bioelectrical signal to be conducted from the skin to the electrode surface by way of the conductive gel in which the tines are embedded. In one embodiment, the conductive gel may be applied to the top surface of the tine array 26 or alternately it may be contained in a sponge which may overlay the tines. A preferred tine height is 0.020"-0.040", however the tine height may range from 0.010"-0.080", ensuring that the tine will efficiently create micro-conduits through the depth of the stratum corneum, while at the same time limiting the amount of deformation of the skin. The decreased height of the tine 24 in combination with small tine size minimizes sensation on the skin during the process of prepping the sensor 12. An adhesive layer, which could be adhesive backed foam, on the perimeter of the electrode 14 may be employed to create a central cavity in which the tine disk is secured. The small size of the tines 24 and the reduced number of times allow the electrode 14 to be worn comfortably for long periods of time. The application procedure does not require specialized training and thus can be performed by any person, including self preparation by the subject of the biopotential recording. Furthermore, it eliminates the need for initial skin preparation by separate abrasive materials or gels prior to electrode application.

In some embodiments, the rigid tine array 26 is formed from a non-conductive material. This same nonconductive material is used to form both the base of the tine array and the tine structures 24 themselves. In an alternate embodiment the tine array material is deposited with conductive particles, such as gold, silver or carbon, to make the part conductive and allow for direct electrode conduction through the structure. Each rigid tine array 26 may have multiple identical or unique tine structures ranging in quantity from 20-60 tines per array. The spacing between the tines 24 is such that the tine array 26 can be adequately machined or molded. For manufacturability, the tines 24 may be aligned in rows or a circular pattern and the orientation of the individual tines 24 may vary. Alternate embodiments may contain tines numbering anywhere between 10 and 100 per array. In addition, the use of tines of various heights may be advantageous to reducing "bed of nails" effect when trying to obtain low skin impedances in certain parts of the body. The differing tine heights may avoid the disadvantage of distributing the applied pressure evenly between identical length tines and thus being unable to pierce the stratum corneum.

Figure 2:
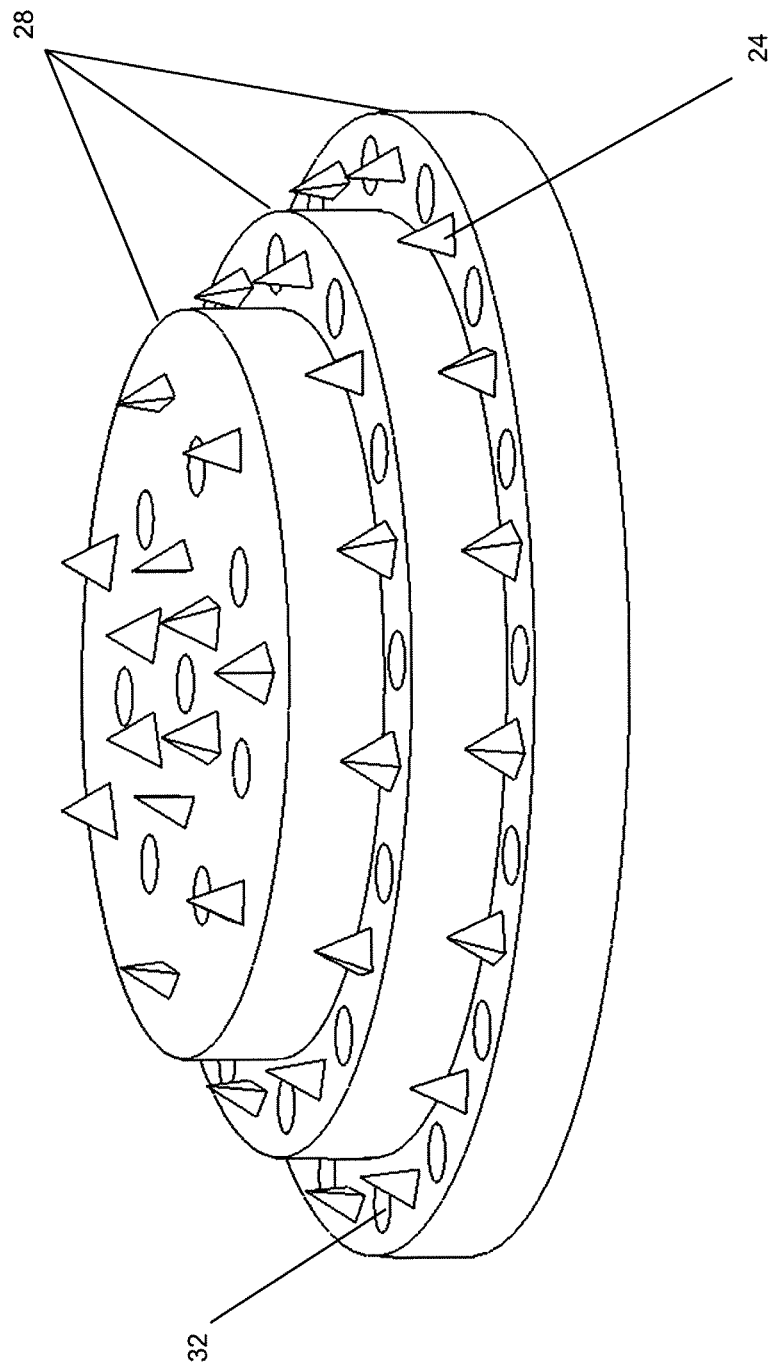
FIG. 2 is a perspective view of one embodiment of a skin preparation device.

The base of the tine array 26 may be flat, convex, or any geometry such that the base conforms to the shape of the skin at the electrode application site. Alternately, the base may be formed in multiple stepped levels 28 as shown in FIG. 2 to allow better displacement or penetration of the stratum corneum at more pliable areas of the skin.

Figure 3A:
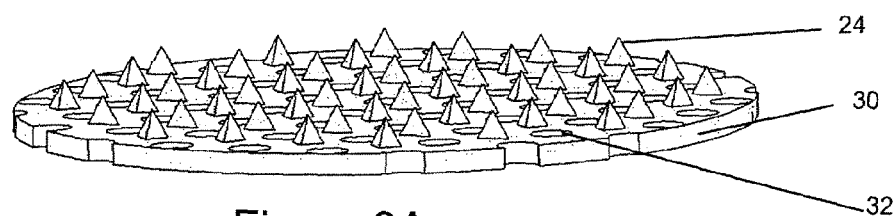
FIG. 3A is a perspective view of a second embodiment of a skin preparation device.
Figure 3B:
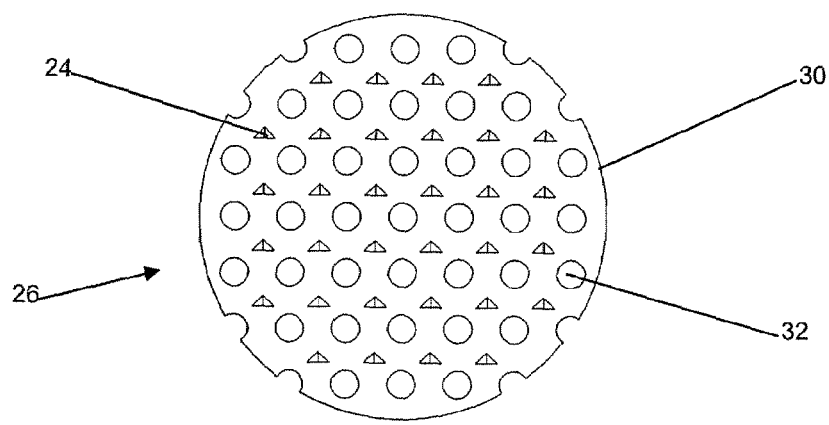
FIG. 3B is a top plan view of the second embodiment of the skin preparation device.
Figure 3C:
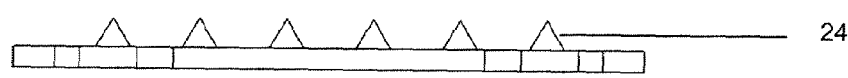
FIG. 3C is a front cross-sectional view of the embodiment of FIG. 3A.
Figure 3D:
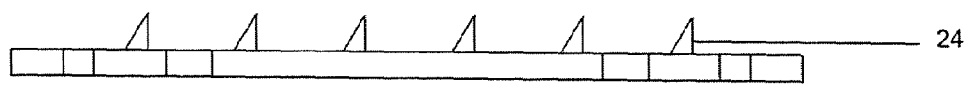
FIG. 3D is a side cross-sectional view of the embodiment of FIG. 3A.

In another embodiment shown in FIG. 3A, the tines 24 are formed on the top surface of the array base. In one embodiment the base 30 of the array 26 is a round disk with a diameter in the range of 0.25"-0.50", however it may range in size from 0.10"-1.0". The shape of the base 30 of the array 26 may also be created in any size and geometry such that the tine array 26 fits within the area of the electrode 14. The base 30 of the tine array 26 may be solid or may contain one or more holes or channels 32. The holes or channels will allow the passage of conductive gel from the surface of the skin to the surface of the electrode.

Figure 4A:
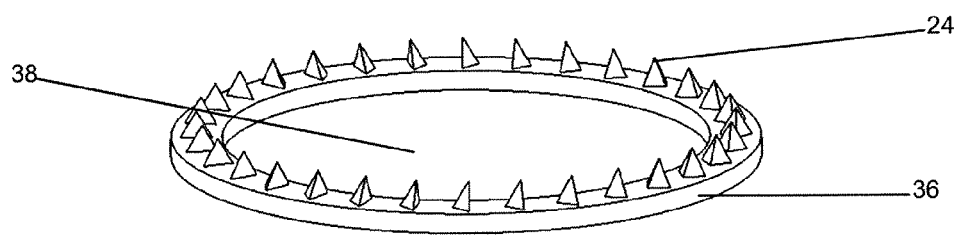
FIG. 4A is a perspective view of a third embodiment of the skin preparation device.
Figure 4B:
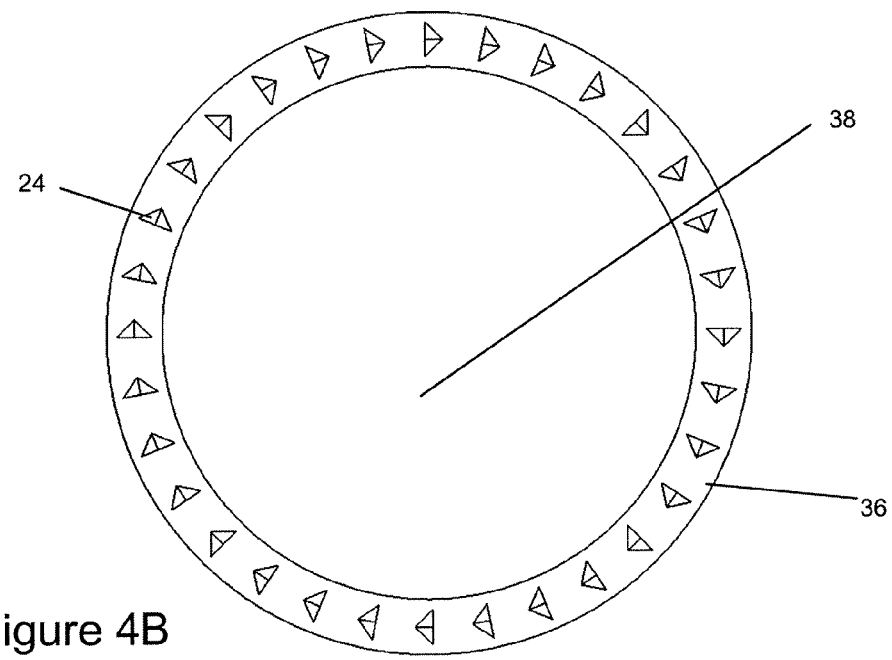
FIG. 4B is a top plan view of the embodiment of FIG. 4A.
Figure 4C:
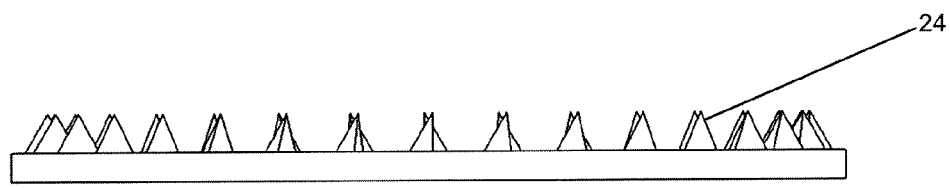
FIG. 4C is a side view of the embodiment of FIG. 4A.
Figure 6:
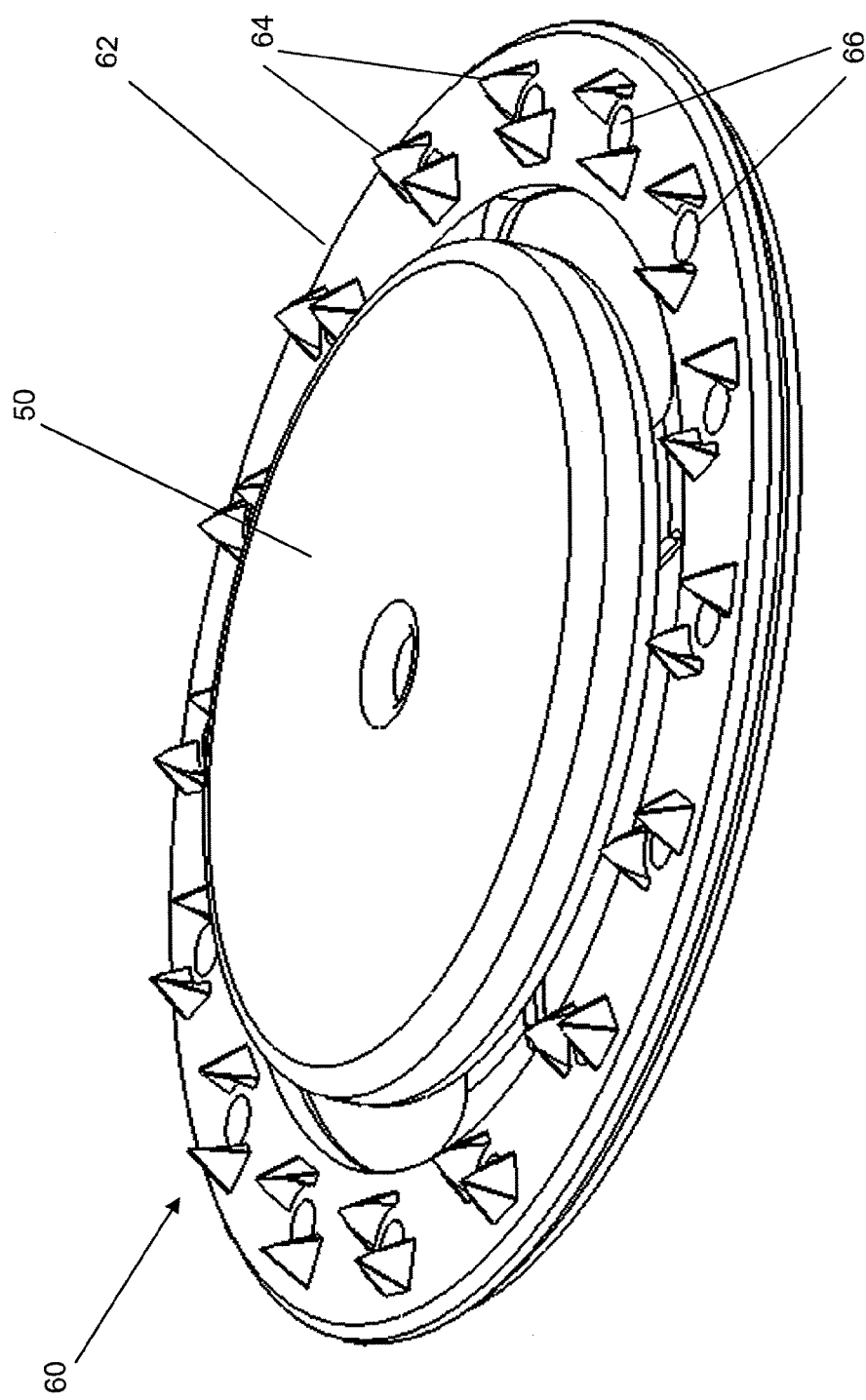
FIG. 6 is a perspective view of an embodiment of a skin preparation device including a separate gel chamber.

An alternate embodiment of the arrangement of the tine array shown in FIG. 4A to 4C is a solid annular ring 36 which contains the tines 24 and which includes a central opening 38 to permit gel flow and electrical contact between the conductive medium and the electrode surface (FIG. 4A). Yet another alternate embodiment has a small round tine array that leaves an outer ring of the electrode surface exposed. Alternate embodiments may contain electrode surfaces up to 1.5" in diameter. In yet another embodiment, the gel may be contained in a separate cavity during storage and gets displaced to the skin site during application or during the prepping action (FIG. 6).

The tine structure is preferably created from a plastic such as polycarbonate (PC), acrylonitrile butadiene styrene (ABS), nylon, etc., through the process of injection molding. In the preferred embodiment the tine structure is created from liquid crystal polymer (LCP), such as Vectra E130i manufactured by Ticona Engineering Polymers, Florence, Ky. The material may alternatively be any nonconductive plastic which is rigid, such that the tips do not bend upon contact with the skin; however, this material, as applied to the structure, must not be brittle, in order to prevent breakage of the tips in the skin. The entire tine array structure may be created through injection molding using the same material in a single piece for both the base 30 and individual tines 24. Alternately, the tine array may be assembled from multiple molded pieces. The use of nonconductive material ensures that offset voltages are not created by contact between metal and skin. The preferred manufacturing method is injection molding due to repeatability and low cost of mass production and the preferred array shape of a disk is optimal for efficiency of injection molding techniques. However, the tine array 26 may be formed by machining, etching or printing methods. An alternate embodiment may include the impregnation of the molded material with carbon nanotubes in order to increase the hardness of the tines 24. The carbon nanotubes may also make the electrode surface partly conductive, which aids in signal acquisition.

Figure 5A:
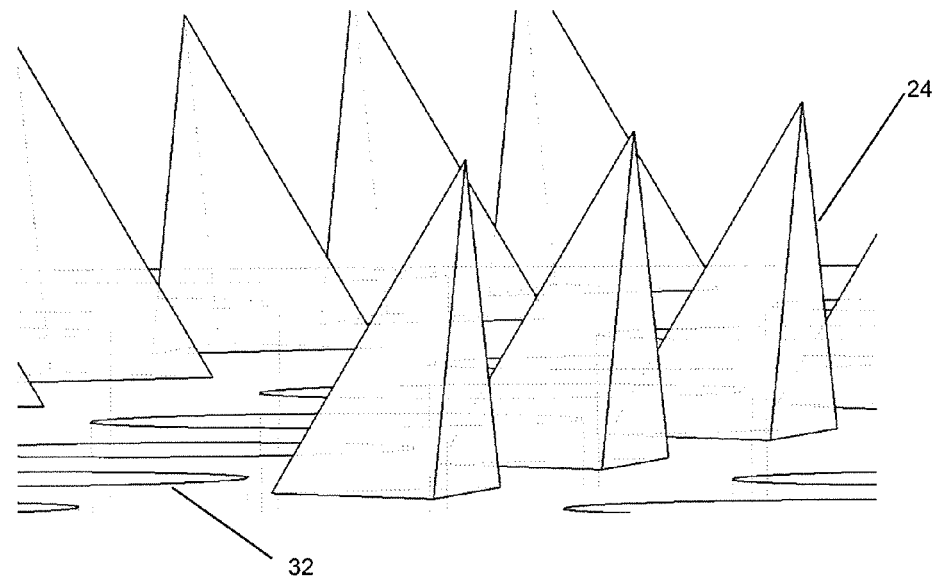
FIG. 5A is an enlarged perspective view of an embodiment of the tines of a skin preparation device.
Figure 5B:
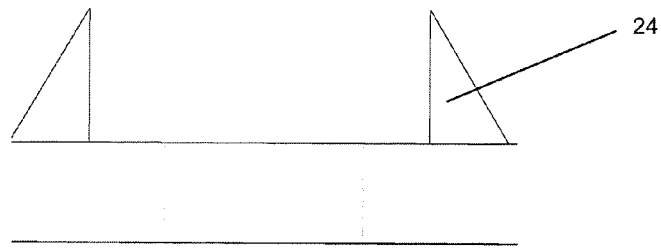
FIG. 5B is a side view of the tines shown in FIG. 5A.
Figure 5C:
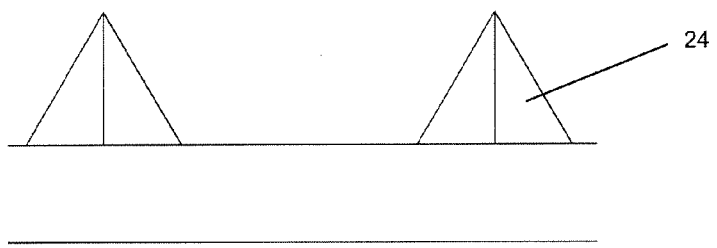
FIG. 5C is a front view of the tines shown in FIG. 5A.

As shown in FIGS. 5A to 5C, each individual tine 24 is generally tapered from base to tip and protrudes in a perpendicular direction from the base. Thus, the tip of each tine 24 penetrates approximately at a 90 degree angle to the skin upon pressing of the electrode against the surface of the skin. Rigid, perpendicular penetration effectively creates repeatable micro-conduits in the stratum corneum with the least force required. The geometry, including the aspect ratio of the tine, is determined to optimize the sharpness of the tip, the effectiveness of skin penetration and the manufacturability of the device. The sharpness of the tip of the tine 24 can be quantified as a radius of curvature. The tines 24 in the arrays 26 have a radius of curvature less than 0.02". Additionally, the height of an individual tine may be in the range of 0.010"-0.080" though the preferred height is in the range of 0.020"-0.040". The preferred geometry of the tine 24 is that of a triangular pyramid with an isosceles triangle shaped base. The base of the triangular pyramid may also be an equilateral or scalene triangle. The geometry of the tine 24 may be various other shapes which allow for a taper from base to tip such as a rectangular pyramid, a half cone with a semicircular base or a full cone with a full circle or an elliptical base, or the tine 24 can be in the shape of an obelisk where the taper does not necessarily begin at the base of the tine. In a preferred embodiment, one face of the pyramid, preferably the face corresponding to the longest side of the triangle may extend at a 90 degree angle from the base.

As shown in FIG. 5B, the cross section of such a tine would be a right-angled triangle having one side as vertical, that is, perpendicular to the base.

Impedance measurements at the skin interface were obtained with a biopotential sensor consisting of an array of four (4) electrodes (in an arrangement as shown in FIG. 1B) each including an embodiment of the rigid tine device. This embodiment of the tine device consisted of an array of twenty four (24) pyramidal tines at 0.030" in height, and with a sharp point having a radius of curvature less than 0.01". The measurements averaged 7 kΩ with less than 2.6 kΩ standard deviation across subjects.

Referring to FIG. 1B, an implementation of the skin prepping device is shown in a sensor array. Each electrode area 14 contains multiple tine arrays 26 which are arranged over a layer of conductive material. The prepping structures or tine arrays 26 are arranged on the individual electrodes 14 such that a substructure is created with independent prepping areas. When the individual electrodes 14 with the created substructure of tine arrays 26 are pressed upon, in order to prep the skin, the tine arrays 26 approach the skin at different angles. The angulations of the individual tine arrays 26 accommodate skin irregularities in certain areas of the body or in the softer tissue areas.

In an alternate embodiment, shown in FIG. 6, an exemplary gel storage container or chamber 50 is shown coupled to a prepping device 60. In certain embodiments, the gel storage container may be a burst container. The burst container is designed to open upon the application of force. The gel storage container 50 will hold the conductive gel separate from the electrode and prepping mechanism until the sensor is applied to a patient's skin. This will aid in a longer shelf life for the sensor since any dryout by the conductive gel will be avoided during storage. The gel storage container 50 is shown with a ring prepping mechanism, however, the gel storage container may be used in combination with any of the skin preparation mechanisms shown. In the illustrated embodiment of FIG. 6, the prepping mechanism includes a base member 62 that is contiguous with a plurality of generally pyramidal tines 64. Each tine 64 may have a concave side that is aligned with a curved sidewall of an aperture or hole 66 formed in the base member 62 of the prepping device 60. In some embodiments, the gel storage container is designed such that applying pressure on the skin prepping device causes the gel to flow from the gel storage device through the aperture into the area between the prepping device and the skin. This serves to precisely place the gel at the site of the micro conduits created by the time arrays.

Figure 7A:
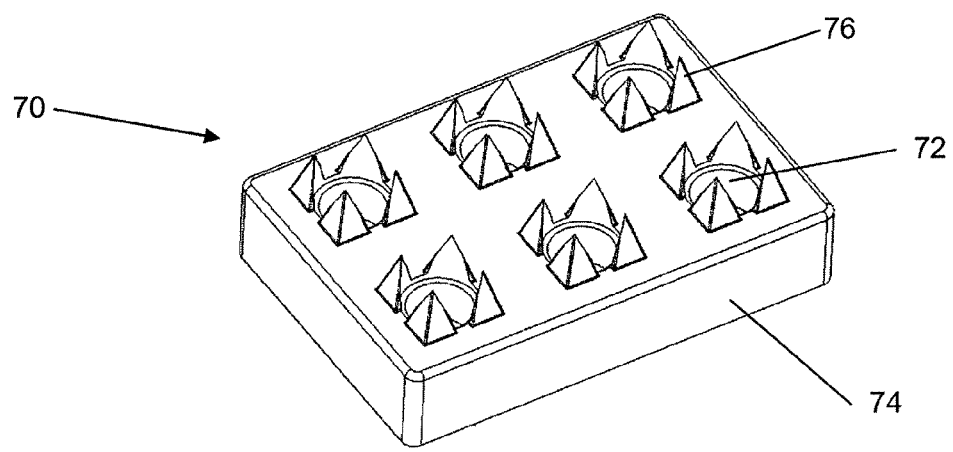
FIG. 7A is a perspective view of an embodiment of a skin preparation device.
Figure 7B:
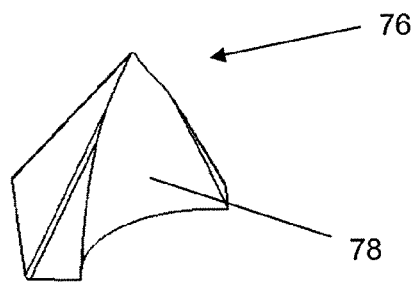
FIG. 7B is an enlarged perspective view of a tine of the embodiment shown in FIG. 7A.

Turning now to FIG. 7A, an alternate prepping mechanism or device 70 is shown. The prepping device 70 may include a plurality of holes or apertures 72 formed in a base member 74. The base member 74 is shown as rectangular in shape, but other shapes may be used. The base member 74 may also include a plurality of tines 76. Each tine 76 is generally pyramidal in shape having a concave side wall. In the preferred embodiment, the concave sidewall is perpendicular to the base of the pyramid as shown in FIG. 7B. This tine construction of a pyramid with a perpendicular concave wall creates a much sharper edge than a pyramid alone, as is evident by the smaller radius of the tip of the preferred construction in comparison to an equivalently-sized pyramid without a concave wall. The concave sidewall of the tine 76 is aligned with a sidewall of one of the apertures 72 in the base member 74. Although, the illustrated embodiment of FIG. 7A shows four tines 76 for each aperture 72, any number of tines 76 may be provided for each aperture 72.

In FIG. 7B, an enlarged drawing of a generally pyramidal tine 76 is shown. The concave sidewall 78 is shown as extending from the apex of the pyramid through the base of the pyramid. This curved sidewall 78 may be aligned with an aperture formed in the base member 74.

Figure 7C:
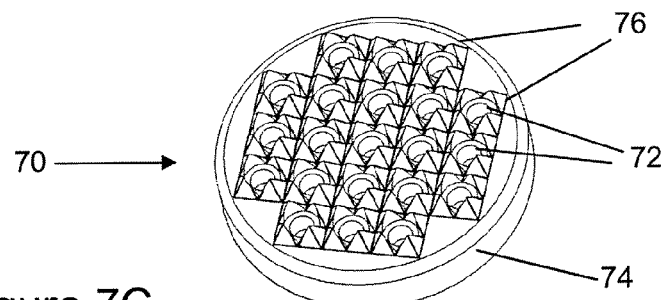
FIG. 7C is an alternate embodiment of the skin preparation device shown in FIG. 7A.

In FIG. 7C, an alternate embodiment of a prepping device or mechanism 70 including the generally pyramidal tines 76 is shown. In this embodiment, an exemplary tine pattern is shown. The tines 76 in combination with the apertures 72 is shown in a cross pattern. Any pattern using the combination of tines 76 and apertures 72 formed in the base member 74 may be used to form a prepping device or mechanism. The pattern shown here is one example of a pattern that is contemplated.

While the foregoing invention has been described with reference to its preferred embodiments, various alterations and modifications may occur to these skilled in the art. All such alterations and modifications are intended to fall within the scope of the appended claims.

What is claimed is:

1. A sensor system comprising:
a flexible substrate;
a plurality of electrodes coupled to the flexible substrate;
an adhesive substrate adjacent to each of the electrodes and the flexible substrate; and a plurality of groups of preparation devices, each group of preparation devices coupled to a respective electrode, each of the preparation devices comprising:
  a base member in the shape of a ring;
  an array of rigid tines contiguous with the base member, each tine having a sharp tip adapted to penetrate stratum corneum and to reduce skin impedance; and
  a component configured to deliver a conductive gel below the stratum corneum.

2. The sensor system of claim 1 wherein the preparation devices are arranged such that upon application of pressure to the electrode, the preparation devices angle to adjust to the surface to which the sensor system is applied.

3. A sensor system comprising:
a flexible substrate;
a plurality of electrodes coupled to the flexible substrate;
an adhesive substrate adjacent to each of the electrodes and the flexible substrate; and
a plurality of groups of preparation devices, each group of preparation devices coupled to a respective electrode, each of the preparation devices comprising:
  a base member;
  an array of rigid tines contiguous with the base member, each tine having a sharp tip adapted to penetrate stratum corneum and to reduce skin impedance;
  a component configured to deliver a conductive gel below the outermost layer of the stratum corneum; and
  wherein the base member is formed of multiple stepped levels each level containing a portion of the array of rigid tines.

4. The sensor system of claim 3 wherein the preparation devices are arranged such that upon application of pressure to the electrode, the preparation devices angle to adjust to the surface to which the sensor system is applied.

5. A sensor system comprising:
a flexible substrate;
a plurality of electrodes coupled to the flexible substrate;
an adhesive substrate adjacent to each of the electrodes and the flexible substrate; and
a plurality of groups of preparation devices, each group of preparation devices coupled to a respective electrode, each of the preparation devices comprising:
  a base member; and
  an array of tines contiguous with the base member, each tine having a pyramidal shape wherein one side of the pyramid is concave.

6. The sensor system of claim 5 wherein the preparation devices are arranged such that upon application of pressure to the electrode, the preparation devices angle to adjust to the surface to which the sensor system is applied.

7. A sensor system comprising:
a flexible substrate;
a plurality of electrodes coupled to the flexible substrate;
an adhesive substrate adjacent to each of the electrodes and the flexible substrate; and
a plurality of groups of preparation devices, each group of preparation devices coupled to a respective electrode, each of the preparation devices comprising:
  a base member; and
  an array of rigid tines contiguous with the base member, each tine having a sharp tip adapted to penetrate stratum corneum and to reduce skin impedance.

8. The sensor system of claim 7 wherein the preparation devices are arranged such that upon application of pressure to the electrode, the preparation devices angle to adjust to the surface to which the sensor system is applied.

* * * * *